United States Patent
Yang et al.

(10) Patent No.: US 11,279,699 B2
(45) Date of Patent: Mar. 22, 2022

(54) COMPOUND AS SELECTIVE JAK INHIBITOR, AND SALT AND THERAPEUTIC USE THEREOF

(71) Applicant: Suzhou Longbiotech Pharmaceuticals Co., Ltd., Suzhou (CN)

(72) Inventors: Hengying Yang, Suzhou (CN); Sheng Kuang, Suzhou (CN); Shiwei Li, Suzhou (CN); Kuiwang Wu, Suzhou (CN); Shuxin Li, Suzhou (CN)

(73) Assignee: Suzhou Longbiotech Pharmaceuticals Co., Ltd., Suzhou (CN)

( * ) Notice: Subject to any disclaimer, the term of this patent is extended or adjusted under 35 U.S.C. 154(b) by 89 days.

(21) Appl. No.: 16/320,796

(22) PCT Filed: Jul. 25, 2017

(86) PCT No.: PCT/CN2017/094254
§ 371 (c)(1),
(2) Date: Jan. 25, 2019

(87) PCT Pub. No.: WO2018/019223
PCT Pub. Date: Feb. 1, 2018

(65) Prior Publication Data
US 2020/0190080 A1 Jun. 18, 2020

(30) Foreign Application Priority Data

Jul. 26, 2016 (CN) .......................... 201610590791.7
Jan. 19, 2017 (CN) .......................... 201710037675.7

(51) Int. Cl.
| | | |
|---|---|---|
| C07D 471/04 | (2006.01) | |
| A61P 37/02 | (2006.01) | |
| C07D 487/04 | (2006.01) | |
| A61P 35/00 | (2006.01) | |
| A61P 29/00 | (2006.01) | |
| C07D 401/04 | (2006.01) | |
| A61P 17/00 | (2006.01) | |
| A61P 19/02 | (2006.01) | |

(52) U.S. Cl.
CPC ............ *C07D 471/04* (2013.01); *A61P 17/00* (2018.01); *A61P 19/02* (2018.01); *A61P 29/00* (2018.01); *A61P 35/00* (2018.01); *A61P 37/02* (2018.01); *C07D 401/04* (2013.01); *C07D 487/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 7,598,257 | B2 | 10/2009 | Rodgers et al. |
| 2007/0207995 | A1 | 9/2007 | Salituro et al. |
| 2007/0208053 | A1 | 9/2007 | Arnold et al. |
| 2009/0088445 | A1 | 4/2009 | Ledeboer et al. |
| 2010/0311693 | A1 | 12/2010 | Curry et al. |
| 2010/0331319 | A1 | 12/2010 | Menet |
| 2011/0190260 | A1 | 8/2011 | Menet et al. |
| 2012/0277247 | A1 | 11/2012 | Menet et al. |

FOREIGN PATENT DOCUMENTS

| | | |
|---|---|---|
| CN | 101228161 A | 7/2008 |
| CN | 101374839 A | 2/2009 |
| CN | 101448826 A | 6/2009 |
| CN | 101801971 A | 8/2010 |
| CN | 102026999 A | 4/2011 |
| CN | 102105471 A | 6/2011 |
| CN | 102459258 A | 5/2012 |
| CN | 102482273 A | 5/2012 |
| CN | 103254190 A | 8/2013 |
| CN | 103764654 A | 4/2014 |
| CN | 106905322 A | 6/2017 |
| CN | 107531695 A | 1/2018 |
| EP | 2343299 A1 | 7/2011 |

(Continued)

OTHER PUBLICATIONS

American Chemical Society. Chemical Abstract Service. RN 1269210-01-6. Entered into STN: Mar. 21, 2011. (Year: 2011).*
American Chemical Society. Chemical Abstract Service. RN 1609835-65-5. Entered into STN: Jun. 6, 2014. (Year: 2014).*
Office Action issued by the Chinese Patent Office in the Chinese application No. 201780044487.5 and its English translation; dated Dec. 29, 2020.
Office Action issued by the Chinese Patent Office in the Chinese application No. 201780044794.3 and its English translation; dated Jan. 7, 2021.

(Continued)

*Primary Examiner* — John S Kenyon
(74) *Attorney, Agent, or Firm* — Fox Rothschild LLP

(57) ABSTRACT

Disclosed are a compound as a selective JAK inhibitor, and an isomer, a solvate or a pharmaceutically acceptable salt thereof, wherein: the definitions of (A), R, $R^1$ and n are described in detail in the specification. In addition, also disclosed are a medicament including the compound and salts thereof as an active ingredient, and the use thereof in the preparation of a medicament for treating JAK-related target diseases, such as immune system diseases, rheumatoid arthritis and tumors.

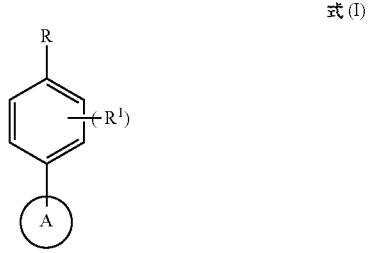

8 Claims, No Drawings

(56) References Cited

FOREIGN PATENT DOCUMENTS

| | | |
|---|---|---|
| EP | 2445912 B1 | 8/2014 |
| EP | 1973911 B1 | 1/2016 |
| EP | 2288610 B1 | 8/2016 |
| EP | 2445911 B1 | 3/2017 |
| EP | 3290418 A1 | 3/2018 |
| EP | 3409673 A1 | 12/2018 |
| EP | 3492469 A1 | 6/2019 |
| JP | 2009519340 A | 5/2009 |
| JP | 2009523812 A | 6/2009 |
| JP | 2009532475 A | 9/2009 |
| JP | 2011529032 A | 12/2011 |
| JP | 2012528886 A | 11/2012 |
| JP | 2012530766 A | 12/2012 |
| JP | 2014512405 A | 5/2014 |
| JP | 2019503395 A | 2/2019 |
| WO | 2007041130 A2 | 4/2007 |
| WO | 2007070514 A1 | 6/2007 |
| WO | 2007084557 A2 | 7/2007 |
| WO | 2007084667 A2 | 7/2007 |
| WO | WO-2007084667 A2 * 7/2007 .............. A61P 19/02 |
| WO | 2007117494 A1 | 10/2007 |
| WO | 2009114512 A1 | 9/2009 |
| WO | 2010010184 A1 | 1/2010 |
| WO | 2010010186 A1 | 1/2010 |
| WO | 2010010190 A1 | 1/2010 |
| WO | 2010141796 A2 | 12/2010 |
| WO | 2012146659 A1 | 11/2012 |
| WO | 2013019828 A1 | 2/2013 |
| WO | 2013173506 A2 | 11/2013 |
| WO | 2016173484 A1 | 11/2016 |
| WO | 2017129116 A1 | 8/2017 |

OTHER PUBLICATIONS

Christel J. Menet et al. "Triazolopyridines Selective JAK1 Inhibitors: From Hit Identification to GLPG0634"J. Med. Chem. vol. 57, Nov. 4, 2014 pp. 9323-9342.

Database Registry [Online], Chemical Abstracts Service, (2012); Database accession No. 1360287-34-8, Abstract, 1 pg.

Supplementary European Search Report from related European Application No. 17 83 3525, dated Mar. 2, 2020; 27 pgs.

NPL1-Database Registry [Online] Chemical Abstracts Service, Columbus, Ohio, US; Jun. 6, 2014 (Jun. 6, 2014), "7H-Pyrrolo[2,3-d]pyrimidine, 4-[4-[1-(1-piperidinyl)ethyl]phenyl]-", XP002793677, Database accession No. 1609835-65-5, 1 pg.

NPL2-Database Registry [Online] Chemical Abstracts Service, Columbus, Ohio, US; Mar. 21, 2011 (Mar. 21, 2011), "7H-Pyrrolo[2,3-d]pyrimidine, 4-[4-[1-(4-morpholinyl)ethyl]phenyl]-",XP002793678, Database accession No. 1269210-01-6, 1 pg.

Office Action from related European Application No. 17 833 526.1; 7 pgs.

Office Action dated May 25, 2021 in related JP Apln. No. 2019-504824; 11 pgs.

Office Action dated Jun. 22, 2021 in related JP Apln No. 2019-504825; 16 pgs.

* cited by examiner

COMPOUND AS SELECTIVE JAK INHIBITOR, AND SALT AND THERAPEUTIC USE THEREOF

CROSS REFERENCE TO RELATED APPLICATIONS

The present application is a national application of PCT/CN2017/094254 filed on Jul. 25, 2017, which claims the priorities of the Chinese Patent Application No. 201610590791.7 filed on Jul. 26, 2016 and the Chinese Patent Application No. 201710037675.7 filed on Jan. 19, 2017. The Chinese Patent Applications No. 201610590791.7 and No. 201710037675.7 are incorporated herein by reference as part of the disclosure of the present application.

FIELD OF THE INVENTION

The present disclosure relates to a class of compounds as selective JAK inhibitors, and isomers, solvates, and salts thereof, relates to medicaments containing the said compounds or salts thereof as active ingredients, and relates to use of the compounds in the preparation of medicaments for treating diseases related to JAK targets such as immune system diseases, rheumatoid arthritis and tumors.

BACKGROUND OF THE INVENTION

The JAK-STAT signaling pathway is a cytokine-stimulated signal transduction pathway discovered in recent years, wherein JAK plays an important role in cytokine signaling. The downstream substrates of the kinase JAK family include signal transducers and activators of transcription (STAT). JAK protein is an important member in this pathway, and the abnormal increase in its activity often leads to onset of diseases. Many diseases are related to abnormal cellular responses of JAK-STAT signaling pathway, including autoimmune diseases, inflammatory diseases, bone diseases, metabolic diseases, neurological and neurodegenerative diseases, cancers, cardiovascular diseases, allergy and asthma, and Alzheimer's disease.

Rheumatoid arthritis (RA) is a chronic autoimmune disease commonly observed in clinic, which is mainly characterized by joint swelling, pain, stiffness, deformity and severe functional impairment. The population incidence rate of RA is 0.5%-1.0%. Because the pathogenesis of RA is not clear, its pathological process is difficult to control, and the disability rate is high, which seriously impairs the physical and mental health of patients and reduces the quality of life of patients. The drugs currently used to treat RA are mainly non-steroidal anti-inflammatory drugs (NSAIDs), disease-modifying antirheumatic drugs (DMARDs), and antibody drugs. For a long time, the first-line drugs for the treatment of RA were DMARDs. In 1988, the first DMARD drug methotrexate (MTX) was approved by the FDA for the treatment of RA, rendering MTX an important milestone in the history of RA treatment. The drug is widely used due to its advantages such as effectiveness, tolerability, safety, etc., but it has adverse effects including nausea, vomiting, stomach discomfort, and hepatotoxicity. In contrast, newly developed antibody drugs have good efficacy and safety indicators for moderate to severe RA. However, because it targets specific cytokines, the population benefit from it is significantly limited, and meanwhile the cost of treatment and administration of injection also limit the promotion of such drugs.

In the past 20 years, the treatment of RA has achieved great improvement, and the patient's condition can be effectively controlled by the existing treatment regimen. However, RA patients are yet experiencing problems such as recurrence of the disease, unsatisfactory treatment effect, poor long-term tolerance, and some adverse effects. More importantly, the quality of life of RA patients, including function of organs such as joints, has not been really improved by existing treatments. Therefore, there is still huge unmet clinical needs in this field regarding restoring the normal function of patients.

Studies have shown that the core treatment of RA is the production of a large number of cytokines by autocrine of mononuclear/macrophages, lymphocytes, etc. infiltrated in RA synovial tissue and cells. These cytokines interact and activate JAK/STAT signaling pathway (Januskinase/Signal transducer and activators of transcription signaling pathway) through different ways. By specifically inhibiting the JAK/STAT signaling pathway, the cascade amplification of these cytokines can be blocked, thereby improving the symptoms of damaged joints in RA patients. Therefore, the JAK/STAT signaling pathway is a potential target for the treatment of RA. In November 2012, the oral JAK inhibitor Tofacitinib was first approved by the FDA for the treatment of rheumatoid arthritis (RA), becoming the first successful kinase inhibitor drug in the field.

The JAK-STAT signaling pathway is a cytokine-stimulated signal transduction pathway discovered in recent years, wherein JAK plays an important role in cytokine signaling. JAK kinase (abbreviated as JAKs, including four known members JAK1, JAK2, JAK3, TYK2) is a small family of cytoplasmic non-receptor tyrosine protein kinase superfamilies JAK3 is distributed in the bone marrow and lymphatic system, and JAK1, TYK2, and JAK2 are widely distributed in various tissue cells. When JAKs bind to cytokine receptors on the cell surface, the receptor-coupled JAKs are activated, and in turn the receptors are phosphorylated. This provides a recruitment site for cytoplasmic signal transducers and activators of transcription STAT protein (abbreviated as STAT, including STAT1-4, STAT5a, STAT5b, STAT6). JAKs phosphorylate the STAT protein, and the latter is transferred into the nucleus to regulate gene expression after dimerization. This pathway is JAK/STAT signaling pathway (O'Shea J. J., et al., N. Engl. J. Med., 2013, 368:161-170).

The JAK/STAT signaling pathway is a signaling pathway stimulated by a variety of cytokines and growth factor receptors, including interleukins, interferons (IFN-a, IFN-β, IFN-γ), erythropoietin (EPO), granulocyte-macrophage colony stimulating factor (GM-CSF), somatotropin (GH), prolactin (PRL), thrombopoietin (TPO), etc., which plays a key role in the proliferation of immune cells and hematopoietic stem cells, and the biological process of immune regulation (Ghoreschi K., et al., Immunol. Rev., 2009, 228:273-287).

JAK1 can bind to IL-10, IL-19, IL-20, IL-22, IL-26, IL-28, IFN-a, IFN-γ, IL-6 in the gp130 family, and other receptors containing γc, etc. (Rodig S. J., et al., Cell, 1998, 93:373-383). JAK1 knockout experiments on mouse models indicate that this enzyme plays a key role in regulating the biological effects of the various cytokine receptors described above (Kisseleva T., et al., Gene, 2002, 285:1-24).

JAK1 is a novel target in the field of diseases such as immune-related diseases, inflammation and cancer. JAK1 inhibitors can be used to treat/prevent autoimmune diseases and inflammation (Hornakova T., et al., Blood, 2010, 115: 3287-3295), such as leukemia, lymphoma, melanoma, arthritis, psoriasis, Crohn's disease, lupus erythematosus, acquired immunodeficiency syndrome (Hou S., et al., Hum. Genet., 2013, 132:1049-1058) and the like.

JAK2 plays an important role in the regulation of various receptor signals including IL-3, IFN-γ, EPO, GH and the like (Levy D. E., et al., Nat. Rev. Mol. Cell Biol., 2002, 3:651-662). Knocking out JAK2 in a mouse model can lead to the death of anemia animals (Schindler C., et al., J. Biol. Chem., 2007, 282:20059-20063); a base mutation JAK2V617F on the JAK2 gene in humans is closely related to the occurrence of polycythemia vera (PV) and essential thrombocythemia (ET) in myeloproliferative diseases, etc. (Ghoreschi K., et al., Immunol. Rev., 2009, 228:273-287).

JAK3 regulates cell signaling by binding to the gamma co-chain (γc) in cytokine receptor complexes such as IL-2, IL-4, IL-7, IL-9, IL-15, IL-21. Both JAK3 and γc mutations can lead to severe combined immunodeficiency (SCID) (Villa A., et al., Blood, 1996, 88:817-823). Abnormal JAK3 activity is characterized by a large decrease in T cells and NK cells, and loss of B cell function, which severely affects the normal biological functions of the immune system. Based on its functional characteristics and special tissue distribution, JAK3 has become an attractive drug target for immune system-related diseases. Its inhibitors have great value of clinical application in the treatment/prevention of rheumatoid arthritis (RA), Crohn's disease, systemic lupus erythematosus, multiple sclerosis, type I diabetes, psoriasis, allergic diseases, asthma, chronic obstructive pulmonary disease, leukemia, lymphoma, organ transplantation and other diseases (Papageorgiou A. C., et al., 2004, Trends Pharm. Sci., 2004, 25:558-562).

TYK2 is the first member of the JAK family and can be activated by a variety of receptors such as interferons (IFNs), IL-10, IL-12, IL-23, IL-27, and the like. In mice, loss of TYK2 function can cause defects in the signaling pathways of various cytokine receptors, leading to viral infection, decreased antibacterial and immune function, and increased likelihood of pulmonary infection (Kisseleva T., et al., 2002, Gene, 285:1-24). In addition, studies from the Lamer A. C group have shown that TYK2 can help inhibit the growth and metastasis of breast cancer (Zhang Q., et al., 2011, J. Interferon Cytokine Res., 31:671-677).

Because JAK kinase is involved in various important physiological processes in the body, extensive inhibition of different subtypes may have adverse effects. Tofacitinib is used in patients with moderate to severe RA with insufficient MTX response or intolerance. It was observed that it has certain adverse effects in clinical trials, including infection, tuberculosis, tumor, anemia, liver damage, increased cholesterol and the like. Tofacitinib has significant inhibitory activity on JAK1, JAK2, and JAK3 subtypes. Because JAK2 activity is associated with red blood cell differentiation and lipid metabolism, some of the above adverse effects are thought to be related to the non-selective inhibition profile of the drug. Therefore, the search for selective JAK1 and/or JAK3 inhibitors will become a new direction of RA drug research.

Currently, JAK inhibitors have been proven to be useful in medicaments for the treatment of blood system diseases, tumors, rheumatoid arthritis, psoriasis and the like.

SUMMARY OF THE INVENTION

The first object of this disclosure is to provide a class of selective JAK inhibitor compounds.

In particular, provided herein are a class of selective JAK inhibitor compounds having the structure of formula (I):

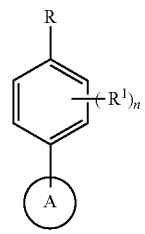

Formula (I)

and an isomer, a solvate or a pharmaceutically acceptable salt thereof;

when

is selected from:

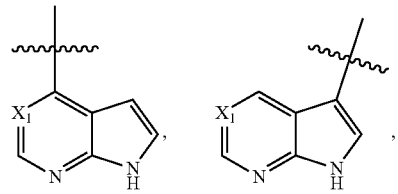

R is selected from:

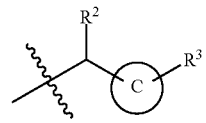

wherein:

is a 4-10 membered nitrogen-containing heterocycle wherein the carbon atom can be replaced by O, S, or —SO$_2$—;

$R^1$ is hydrogen, $C_1$-$C_6$ alkyl, or halogen;

$R^2$ is hydrogen or $C_1$-$C_3$ alkyl;

$R^3$ is hydrogen, $C_1$-$C_3$ alkyl, or $C_1$-$C_6$ alkylsulfonyl;

n is selected from 0, 1, 2;

When

is selected from:

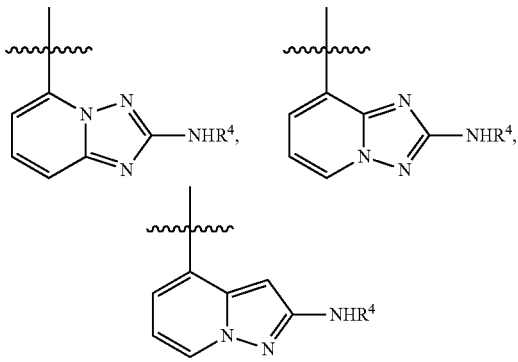

wherein:

Ⓒ is selected from:

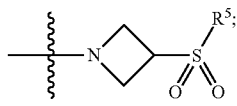

R¹ is hydrogen, $C_1$-$C_6$ alkyl, or halogen;
R⁴ is hydrogen, $C_1$-$C_7$ alkylacyl, $C_3$-$C_7$ cycloalkylacyl, or a $C_1$-$C_6$ alkylsulfonyl, and may be optionally substituted by $C_1$-$C_6$ alkoxy, $C_1$-$C_6$ alkylsulfonyl, or halogen;
R⁵ is selected from $C_1$-$C_5$ alkyl, $C_3$-$C_7$ cycloalkyl, and may be optionally substituted by halogen;
n is selected from 0, 1, 2;
or a pharmaceutically acceptable salt or a solvate thereof.

More preferably, preferred compounds of the structure of formula (I) disclosed herein are:
N-(5-(4-((3-(methylsulfonyl)azetidin-1-yl)methyl)phenyl)-[1,2,4]triazolo[1,5-a]pyridin-2-yl]cyclopropanecarboxamide;
N-(5-(3-fluoro-4-((3-(methylsulfonyl)azetidin-1-yl)methyl) phenyl)-[1,2,4]triazolo[1,5-a]pyridin-2-yl]cyclopropanecarboxamide;
N-(5-(3,5-difluoro-4-((3-(methylsulfonyl)azetidin-1-yl) methyl)phenyl)-[1,2,4]triazolo[1,5-a]pyridin-2-yl]cyclopropanecarboxamide;
N-(5-(4-((3-(methylsulfonyl)azetidin-1-yl)methyl)phenyl)-[1,2,4]triazolo[1,5-a]pyridin-2-yl]isobutyramide;
N-(5-(4-((3-(cyclopropylsulfonyl)azetidin-1-yl)methyl)phenyl)-[1,2,4]triazolo[1,5-a]pyridin-2-yl]isobutyramide;
N-(5-(4-((3-(ethylsulfonyl)azetidin-1-yl)methyl)phenyl)-[1,2,4]triazolo[1,5-a]pyridin-2-yl]isobutyramide;
N-(5-(4-((3-(ethylsulfonyl)azetidin-1-yl)methyl)phenyl)-[1,2,4]triazolo[1,5-a]pyridin-2-yl]cyclopropanecarboxamide;
5-(4-((3-(methylsulfonyl)azetidin-1-yl)methyl)phenyl)-[1,2,4]triazolo[1,5-a]pyridin-2-ylamine;
N-(8-(4-((3-(methylsulfonyl)azetidin-1-yl)methyl)phenyl)-[1,2,4]triazolo[1,5-a]pyridin-2-yl]cyclopropanecarboxamide;
N-(8-(4-((3-(cyclopropylsulfonyl)azetidin-1-yl)methyl)phenyl)-[1,2,4]triazolo[1,5-a]pyridin-2-yl]cyclopropanecarboxamide;
N-(8-(4-((3-(ethylsulfonyl)azetidin-1-yl)methyl)phenyl)-[1,2,4]triazolo[1,5-a]pyridin-2-yl]cyclopropanecarboxamide;
N-(8-(4-((3-(methylsulfonyl)azetidin-1-yl)methyl)phenyl)-[1,2,4]triazolo[1,5-a]pyridin-2-yl]cyclopropanecarboxamide;
N-(8-(4-((3-(cyclopropylsulfonyl)azetidin-1-yl)methyl)phenyl)-[1,2,4]triazolo[1,5-a]pyridin-2-yl]isobutyramide;
N-(8-(4-((3-(ethylsulfonyl)azetidin-1-yl)methyl)phenyl)-[1,2,4]triazolo[1,5-a] pyridin-2-yl]isobutyramide;
N-(8-(3-fluoro-4-((3-(methylsulfonyl)azetidin-1-yl)methyl) phenyl)-[1,2,4]triazolo[1,5-a]pyridin-2-yl]cyclopropanecarboxamide;
N-(8-(3,5-difluoro-4-((3-(methylsulfonyl)azetidin-1-yl) methyl)phenyl)-[1,2,4]triazolo[1,5-a]pyridin-2-yl]cyclopropanecarboxamide;
8-(4-((3-(methylsulfonyl)azetidin-1-yl)methyl)phenyl)-[1,2,4]triazolo[1,5-a]pyridin-2-ylamine;
8-(4-((3-(ethylsulfonyl)azetidin-1-yl)methyl)phenyl)-[1,2,4]triazolo[1,5-a]pyridin-2-ylamine;
4-(4-(7H-pyrrolo[2,3-d]pyrimidin-4-yl)benzyl)thiomorpholine 1,1-dioxide;
4-(4-(7H-pyrrolo[2,3-d]pyrimidin-4-yl)benzyl)morpholine;
4-(4-((4-methylpiperazin-1-yl)methyl)phenyl)-7H-pyrrolo[2,3-d]pyrimidine;
1-(4-(7H-pyrrolo[2,3-d]pyrimidin-4-yl)benzyl)piperidin-4-one;
4-(4-(pyrrol-1-ylmethyl)phenyl)-7H-pyrrolo[2,3-d]pyrimidine;
4-(4-(1H-pyrrolo[2,3-b]pyridin-4-yl)benzyl)thiomorpholine 1,1-dioxide;
4-(4-(1H-pyrrolo[2,3-b]pyridin-3-yl)benzyl)thiomorpholine 1,1-dioxide;
4-(4-(1H-pyrrolo[2,3-b]pyridin-3-yl)benzyl)morpholine;
3-(4-((4-methylpiperazin-1-yl)methyl)phenyl)-7H-pyrrolo[2,3-b]pyridine;
4-(4-(1H-pyrrolo[2,3-b]pyridin-3-yl)benzyl)piperidin-4-one, or
3-(4-(pyrrol-1-ylmethyl)phenyl)-1H-pyrrolo[2,3-b]pyridine;
and isomers, solvates or pharmaceutically acceptable salts thereof.

Also provided herein is a pharmaceutical composition comprising the above compound, or isomer, solvate or a pharmaceutically acceptable salt thereof, and pharmaceutically acceptable carriers.

Also provided herein is use of the above compound in the preparation of a medicament for treating a disease associated with JAK kinase.

Preferably, the said use is the use in the preparation of a medicament for treating autoimmune diseases, rheumatoid arthritis, skin conditions, multiple sclerosis, psoriatic arthritis, inflammatory bowel disease, myasthenia gravis, and psoriasis.

Terminology

The term "alkyl" refers to a straight or branched alkyl group having from 1 to 12 carbon atoms in the chain, and examples of the alkyl group include methyl (Me), ethyl (Et), n-propyl, isopropyl, butyl, isobutyl, sec-butyl, tert-butyl (t-Bu), pentyl, isopentyl, tert-pentyl, hexyl, isohexyl, and any group which is considered to be equivalent to the above examples according to those of ordinary skill in the art and the teachings provided herein.

The term "alkoxy" refers to an alkyl group as defined above which is bonded to an oxygen atom. The alkoxy group is attached to the parent structure via the oxygen atom.

The term "amino" refers to a —NH$_2$ group or a mono- or di-alkylamino group.

The term cycloalkyl refers to a saturated and partially saturated, monocyclic, fused polycyclic, bridged polycyclic, or spiro polycyclic carbocyclic ring having from 3 to 12 ring atoms per ring. Illustrative examples of cycloalkyl groups include the following moieties in suitable bonding form:

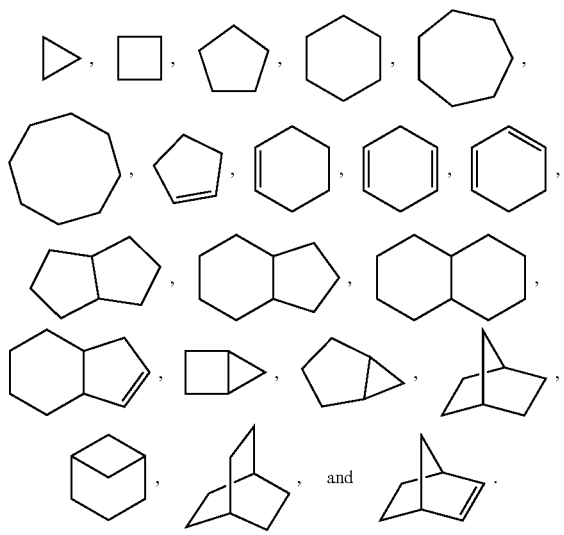

The term "aryl" refers to a 5-6 membered carbo-aromatic ring, such as benzene; bicyclic rings wherein at least one of the rings is a carbo-aromatic ring such as naphthalene, anthracene and 1,2,3,4-tetrahydroquinoline; and tricyclic rings wherein at least one of the rings is a carbo-aromatic ring, such as fluorene.

For example, an aryl group includes a 5-6 membered carbo-aromatic ring fused with a 5-7 membered heterocyclic ring including one or more heteroatoms selected from the group consisting of nitrogen, oxygen, and sulfur, provided that the point of attachment is on the carbo-aromatic ring. A divalent radical is formed by a substituted benzene derivative and a free valence state of the atom on the ring, which is designated as a substituted phenylene radical. A divalent free radical is derived from a monovalent polycyclic hydrocarbon free radical whose name ends with a "radical" by reducing a free valence hydrogen atom, the name being the addition of "ene" after the corresponding monovalent free radical. For example, a naphthyl group having two points of attachment is referred to as a naphthylene group. However, the aryl group does not contain, nor does it overlap in any way with the heterocyclic aryl groups respectively defined below. Thus, as defined herein, if one or more carbo-aromatic rings are attached with a heteroaromatic ring, the resulting ring system is an aromatic heterocyclic group rather than an aryl group.

The term "aromatic heterocyclic group" refers to:
a 5-8 membered monocyclic aromatic hydrocarbon containing one or more heteroatoms selected from N, O and S, such as from 1 to 4 heteroatoms, and in some embodiments, from 1 to 3 heteroatoms, wherein the other atoms in the ring are carbon atoms;

a 8-12 membered bicyclic aromatic hydrocarbon containing one or more heteroatoms selected from N, O and S, such as from 1 to 4 heteroatoms, and in some embodiments, from 1 to 3 heteroatoms, wherein the other atoms in the ring are carbon atoms and at least one ring is an aromatic ring; and

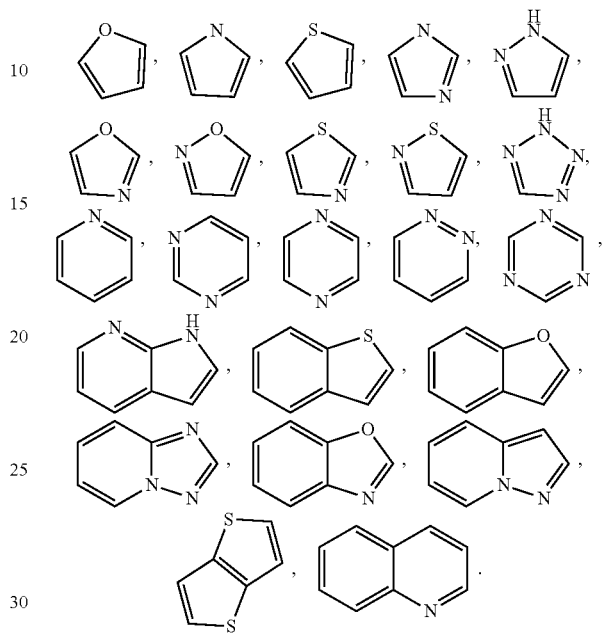

The term "heterocycloalkyl" refers to a saturated or partially unsaturated, monocyclic or polycyclic, cyclic hydrocarbon group comprising from 3 to 20 ring atoms wherein one or more ring atoms are selected from hetero atoms selected from nitrogen, oxygen or S(O)m (where m is an integer from 0 to 2), and the remaining ring atoms are carbon. Preferably, 3 to 12 ring atoms are included, of which 1 to 4 are heteroatoms. More preferably, a heterocycloalkyl ring contains from 3 to 10 ring atoms, and more preferably, a heterocycloalkyl ring contains from 5 to 6 ring atoms. Non-limiting examples of monocyclic heterocycloalkyl groups include pyrrolidinyl, piperidinyl, morpholinyl, tetrahydrofuranyl and the like. Polycyclic heterocycloalkyl groups include spiro, fused, and bridged heterocycloalkyl groups. The heterocyclic ring may be substituted or unsubstituted, and when substituted, the substituent is preferably one or more of the following groups independently selected from alkyl, haloalkyl, alkoxy, alkylamino, halogen, hydroxyl, amino, oxo, alkylamino, cycloalkyl, heterocycloalkyl, heterocycloalkoxy, hydroxyalkyl, carboxy or carboxylate.

The term "halogen" means chlorine, fluorine, bromine or iodine. The term "halo" means chloro, fluoro, bromo or iodo. The term "haloalkyl" refers to an alkyl group as defined above which is substituted by one or more halogen atoms.

The term "haloalkoxy" refers to an alkoxy group as defined above which is substituted by one or more halogen atoms.

The term "acyl" refers to a R—C(O)— group of a straight, branched, or cyclic configuration or a combination thereof having 1 to 10 carbon atoms, which is attached to the parent structure through a hydroxy function group. Such group may be saturated or unsaturated, and aliphatic or aromatic.

In the embodiments provided herein, if the compound disclosed herein contains a basic group, it can form a salt with an acid, and a salt of a pyrimidine derivative can be produced by a method well known to those skilled in the art.

Common acid salts include organic acid salts, inorganic acid salts, and the like. In general, the commonly used organic acid salts are citrate, fumarate, oxalate, malate, lactate, sulfonate (e.g., camphor sulfonate, p-toluenesulfonate, methanesulfonate, and the like), etc.; inorganic acid salts include hydrohalides, sulfates, phosphates, nitrates, and the like.

For example, a lower alkylsulfonic acid such as methanesulfonic acid, trifluoromethanesulfonic acid or the like may form a mesylate salt, a triflate salt; and an arylsulfonic acid such as benzenesulfonic acid, p-toluenesulfonic acid or the like may form p-toluenesulfonate, benzenesulfonate; an organic carboxylic acid such as acetic acid, fumaric acid, tartaric acid, oxalic acid, maleic acid, malic acid, succinic acid, citric acid or the like may form corresponding salts; an amino acid such as glutamic acid or aspartic acid can form glutamate or aspartate. An inorganic acid such as hydrohalic acids (such as hydrofluoric acid, hydrobromic acid, hydroiodic acid, hydrochloric acid), nitric acid, carbonic acid, sulfuric acid or phosphoric acid or the like may also form corresponding salts.

In a second aspect, provided herein is a medicament which utilizes the JAK inhibitor compound of the formula (I), an isomer or a pharmaceutically acceptable salt or a solvate thereof as an active ingredient. The above medicament may further comprise one or more pharmaceutically acceptable carriers, including conventional diluents, excipients, fillers, binders, wetting agents, disintegrants, absorption promoters, surfactants, adsorption carriers, lubricants, etc. in the pharmaceutical field. If necessary, flavoring agents, sweeteners or the like may be added. The medicament disclosed herein can be prepared into various forms such as tablets, powders, granules, capsules, oral liquids and injectable preparations, and the medicaments in the above various dosage forms can be prepared according to a conventional method in the pharmaceutical field.

In a third aspect, provided herein are a JAK inhibitor compound of formula (I), and a pharmaceutically acceptable salt thereof, for use in the medicament for the treatment of autoimmune diseases, rheumatoid arthritis, skin conditions, multiple sclerosis, rheumatoid arthritis, psoriatic arthritis, inflammatory bowel disease, myasthenia gravis, and psoriasis in human or animal, especially for use in the medicament for the treatment of JAK kinase-related diseases.

The inventors of the present disclosure have confirmed by experiments that this product has a good inhibitory effect on JAK kinase, especially JAK1 or JAK3, and has low inhibitory activity on JAK2, suggesting that this product is a selective JAK inhibitor. A medicament using a compound of the formula (I), an isomer or a pharmaceutically acceptable salt thereof has lower toxicity in the treatment of autoimmune diseases, rheumatoid arthritis, skin conditions, multiple sclerosis, rheumatoid arthritis, psoriatic arthritis, inflammatory bowel disease, myasthenia gravis, and psoriasis.

DETAILED DESCRIPTION OF THE SPECIFIC EMBODIMENTS

The practicability of the present disclosure are described below by way of examples, and those skilled in the art will understand that modifications or substitutions of the corresponding technical features are still within the scope of the claimed invention.

Example 1. N-(5-(4-((3-(methylsulfonyl)azetidin-1-yl)methyl)phenyl)-[1,2,4]triazolo[1,5-a]pyridin-2-yl]cyclopropanecarboxamide

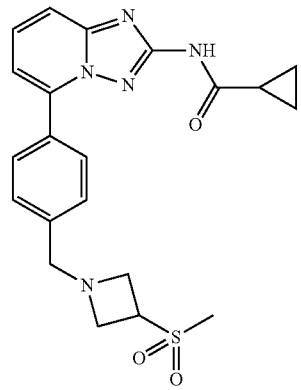 [SMILES: CS(=O)(=O)C1CN(Cc2ccc(-c3cccc4nc(NC(=O)C5CC5)nn34)cc2)C1]

Step 1,
1-(6-bromo-pyridin-2-yl)-3-ethoxycarbonyl-thiourea 10 g of 2-amino-6-bromopyridine was dissolved in 100 ml of dichloromethane, and cooled to 5° C. in an ice bath. 6.8 ml of ethoxycarbonyl isothiocyanate was added. The mixture was gradually warmed to room temperature of 20° C., and stirred for 10 hours. After filtration, washing with petroleum ether and drying, a solid (12 g) was obtained.

Step 2, 5-bromo-[1,2,4]triazolo[1,5a]pyridin-2-ylamine

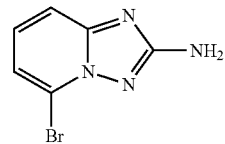 [SMILES: Nc1nc2cccc(Br)n2n1]

10.0 g of hydroxylamine hydrochloride was dissolved in 100 ml of ethanol, 14.5 ml of N,N-diisopropylethylamine was added, and the reaction was stirred at room temperature for 1 hour. 9 g of the product of step 1 was then added, and the mixture was heated under reflux. After 3 hours, the mixture was cooled and solid was precipitated. The solid was filtered, washed, and air-dried to afford 6 g of the desired product.

Step 3. N-(5-bromo-[1,2,4]triazolo[1,5a]pyridin-2-yl)cyclopropanecarboxamide

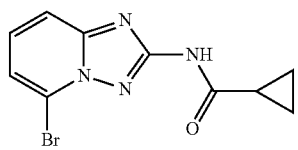 [SMILES: O=C(Nc1nc2cccc(Br)n2n1)C1CC1]

100 ml of dichloromethane and 9 g of diisopropylethylamine were added to 5 g of the product of Step 2. The mixture was cooled to 0° C. in an ice bath. 6.1 g of cyclopropanecarbonyl chloride was added dropwise. The mixture became clear after 1 hour of reaction. After the reaction was continued for 4 hours, the reaction system was concentrated to dryness to give an oily solid. Then, a mixed solution of 7 ml of ammonia water and 43 ml of methanol was added to the oily solid under cooling in an ice salt bath, and stirred for about 3 hours. The system became a brown turbid liquid. After filtration by suction, the solid was washed with water and dried to obtain 4 g of the target.

Step 4, N-(5-(4-((3-(methylsulfonyl) azetidin-1-yl)methyl)phenyl)-[1,2,4]triazolo[1,5-a]pyridin-2-yl]cyclopropanecarboxamide 1 g of N-(5-bromo-[1,2,4]triazolo[1,5-a]pyridin-2-yl)cyclopropanecarboxamide, 1.25 g of 3-(methylsulfonyl)-1-(4,4,5,5-tetramethyl-1,3,2-dioxaborolan-2-yl)benzyl)azetidine, 1.0 g of potassium carbonate, and 0.14 g of Pd(dppf)Cl$_2$ were added in 30 ml of dioxane/water (5:1), and heated to 100° C. for 2 h. After filtration, the filtrate was rotary evaporated to dryness to remove the dioxane and diluted with water. After extracted with ethyl acetate, and purified by column chromatography the title compound (0.86 g) was obtained.

$^1$H NMR (400 MHz, DMSO-D6) δ 9.21 (s, 1H), 7.94 (m, 2H), 7.56-7.62 (m, 2H), 7.44 (m, 2H), 7.26 (s, 1H), 7.07 (d, 1H), 3.94 (m, 1H), 3.77 (s, 2H), 3.60-3.73 (m, 4H), 2.93 (s, 3H), 1.79 (s, 1H), 1.18 (m, 2H), 0.91 (m, 2H). MS (ESI): 426.16 (M+1).

Example 2. N-(5-(3-fluoro-4-((3-(methylsulfonyl)azetidin-1-yl)methyl)phenyl)-[1,2,4]triazolo[1,5-a]pyridin-2-yl]cyclopropanecarboxamide

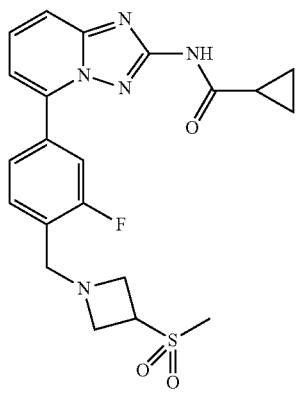 [SMILES: CS(=O)(=O)C1CN(Cc2ccc(-c3cccc4nc(NC(=O)C5CC5)nn34)cc2F)C1]

It was prepared by referring to the method of Example 1.
MS (ESI): 443.15 (M+1)

Example 3. N-(5-(3,5-difluoro-4-((3-(methylsulfonyl)azetidin-1-yl)methyl)phenyl)-[1,2,4]triazolo[1,5-a]pyridin-2-yl]cyclopropanecarboxamide

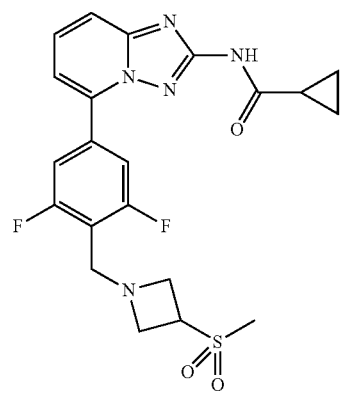 [SMILES: CS(=O)(=O)C1CN(Cc2c(F)cc(-c3cccc4nc(NC(=O)C5CC5)nn34)cc2F)C1]

It was prepared by referring to the method of Example 1.
MS (ESI): 462.14 (M+1)

Example 4. N-(5-(4-((3-(methylsulfonyl)azetidin-1-yl)methyl)phenyl)-[1,2,4]triazolo[1,5-a]pyridin-2-yl]isobutyramide

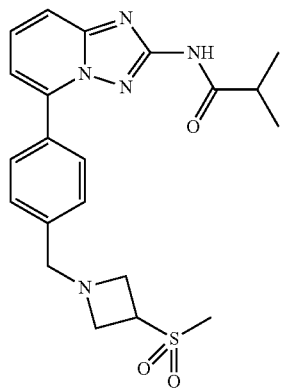 [SMILES: CC(C)C(=O)Nc1nc2cccc(-c3ccc(CN4CC(S(C)(=O)=O)C4)cc3)n2n1]

It was prepared by referring to the method of Example 1.
MS (ESI): 428.17 (M+1)

Example 5. N-(5-(4-((3-(cyclopropylsulfonyl)azetidin-1-yl)methyl)phenyl)-[1,2,4]triazolo[1,5-a]pyridin-2-yl]isobutyramide

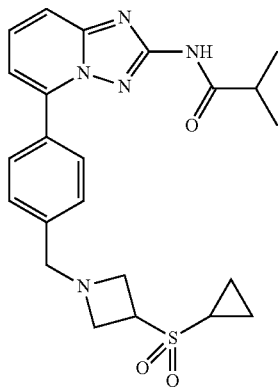 [SMILES: CC(C)C(=O)Nc1nc2cccc(-c3ccc(CN4CC(S(=O)(=O)C5CC5)C4)cc3)n2n1]

It was prepared by referring to the method of Example 1.
MS (ESI): 454.18 (M+1)

Example 6. N-(5-(4-((3-(ethylsulfonyl)azetidin-1-yl)methyl)phenyl)-[1,2,4]triazolo[1,5-a]pyridin-2-yl]isobutyramide

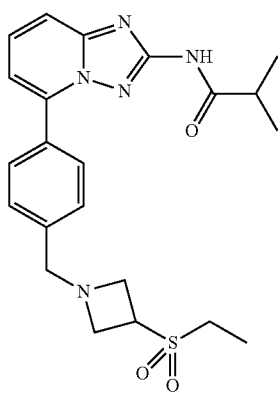 [SMILES: CCS(=O)(=O)C1CN(Cc2ccc(-c3cccc4nc(NC(=O)C(C)C)nn34)cc2)C1]

It was prepared by referring to the method of Example 1.
MS (ESI): 442.18 (M+1)

Example 7. N-(5-(4-((3-(ethylsulfonyl)azetidin-1-yl)methyl)phenyl)-[1,2,4]triazolo[1,5-a]pyridin-2-yl]cyclopropanecarboxamide

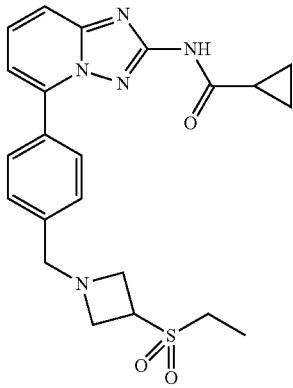

N-(5-(4-((3-(ethylsulfonyl)azetidin-1-yl)methyl)phenyl)-[1,2,4]triazolo[1,5-a]pyridin-2-yl)cyclopropanecarboxamide It was prepared by referring to the method of Example 1.
MS (ESI): 440.17 (M+1)

Example 8. 5-(4-((3-(methylsulfonyl)azetidin-1-yl)methyl)phenyl)-[1,2,4]triazolo[1,5-a]pyridin-2-ylamine

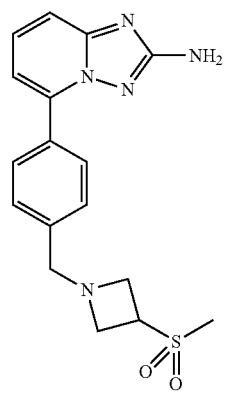 [SMILES: CS(=O)(=O)C1CN(Cc2ccc(-c3cccc4nc(N)nn34)cc2)C1]

1 g of 5-bromo-[1,2,4]triazolo[1,5a]pyridin-2-ylamine, 1.5 g of 3-(methylsulfonyl)-1-(4,4,5,5-tetramethyl-1,3,2-dioxaborolan-2-yl)benzyl)azetidine, 1.0 g of potassium carbonate, and 0.2 g of Pd(dppf)Cl$_2$ were added in 30 ml of dioxane/water (5:1), and heated to 100° C. for 2 h. After filtration, the filtrate was rotary evaporated to dryness to remove the dioxane and diluted with water. After extracted with ethyl acetate, and purified by column chromatography, the title compound (0.86 g) was obtained.

MS (ESI): 358.13 (M+1)

Example 9. N-(8-(4-((3-(methylsulfonyl)azetidin-1-yl)methyl)phenyl)-[1,2,4]triazolo[1,5-a]pyridin-2-yl]cyclopropanecarboxamide

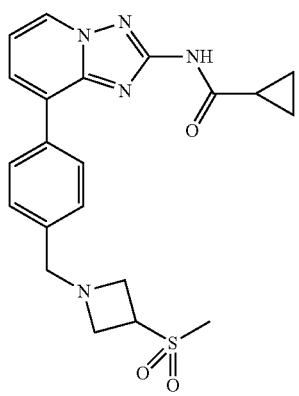 [SMILES: CS(=O)(=O)C1CN(Cc2ccc(-c3cccn4nc(NC(=O)C5CC5)nc34)cc2)C1]

It was prepared by referring to the method of Example 1.
MS (ESI): 426.16 (M+1)

Example 10. N-(8-(4-((3-(cyclopropylsulfonyl)azetidin-1-yl)methyl)phenyl)-[1,2,4]triazolo[1,5-a]pyridin-2-yl]cyclopropanecarboxamide

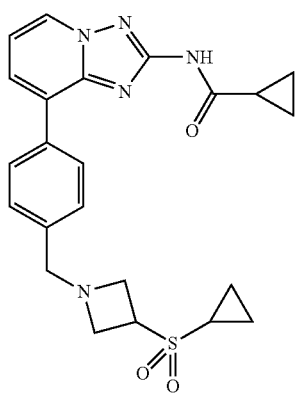 [SMILES: O=C(Nc1nc2c(-c3ccc(CN4CC(S(=O)(=O)C5CC5)C4)cc3)cccn2n1)C1CC1]

It was prepared by referring to the method of Example 1.
MS (ESI): 452.17 (M+1)

Example 11. N-(8-(4-((3-(ethylsulfonyl)azetidin-1-yl)methyl)phenyl)-[1,2,4]triazolo[1,5-a]pyridin-2-yl]cyclopropanecarboxamide

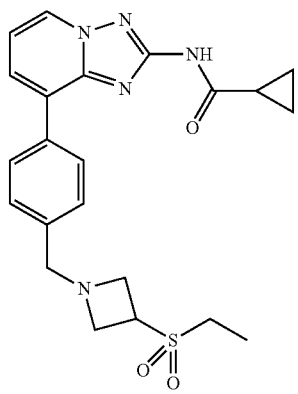 [SMILES: CCS(=O)(=O)C1CN(Cc2ccc(-c3cccn4nc(NC(=O)C5CC5)nc34)cc2)C1]

It was prepared by referring to the method of Example 1.
MS (ESI): 440.17 (M+1)

Example 12. N-(8-(4-((3-(methylsulfonyl)azetidin-1-yl)methyl)phenyl)-[1,2,4]triazolo[1,5-a]pyridin-2-yl]cyclopropanecarboxamide

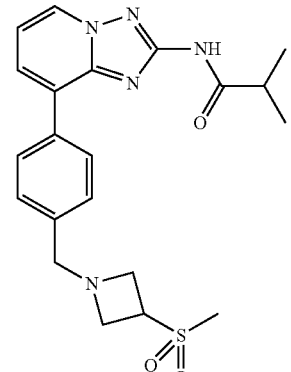

It was prepared by referring to the method of Example 1.
MS (ESI): 428.17 (M+1)

Example 13. N-(8-(4-((3-(cyclopropylsulfonyl)azetidin-1-yl)methyl)phenyl)-[1,2,4]triazolo[1,5-a]pyridin-2-yl)isobutyramide

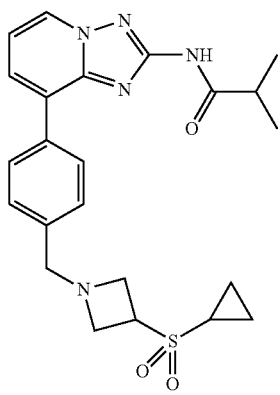 [SMILES: CC(C)C(=O)Nc1nc2c(-c3ccc(CN4CC(S(=O)(=O)C5CC5)C4)cc3)cccn2n1]

It was prepared by referring to the method of Example 1.
MS (ESI): 454.18 (M+1)

Example 14. N-(8-(4-((3-(ethylsulfonyl)azetidin-1-yl)methyl)phenyl)-[1,2,4]triazolo[1,5-a]pyridin-2-yl]isobutyramide

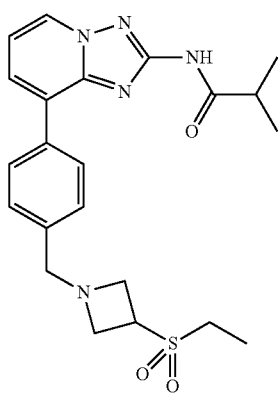 [SMILES: CCS(=O)(=O)C1CN(Cc2ccc(-c3cccn4nc(NC(=O)C(C)C)nc34)cc2)C1]

It was prepared by referring to the method of Example 1.
MS (ESI): 442.18 (M+1)

Example 15. N-(8-(3-fluoro-4-((3-(methylsulfonyl)azetidin-1-yl)methyl)phenyl)-[1,2,4]triazolo[1,5-a]pyridin-2-yl]cyclopropanecarboxamide

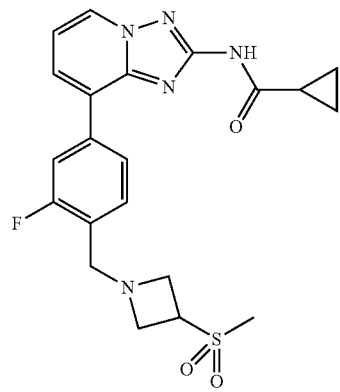 [SMILES: CS(=O)(=O)C1CN(Cc2ccc(-c3cccn4nc(NC(=O)C5CC5)nc34)cc2F)C1]

It was prepared by referring to the method of Example 1.
MS (ESI): 443.15 (M+1)

Example 16. N-(8-(3,5-difluoro-4-((3-(methylsulfonyl)azetidin-1-yl)methyl)phenyl)-[1,2,4]triazolo[1,5-a]pyridin-2-yl]cyclopropanecarboxamide

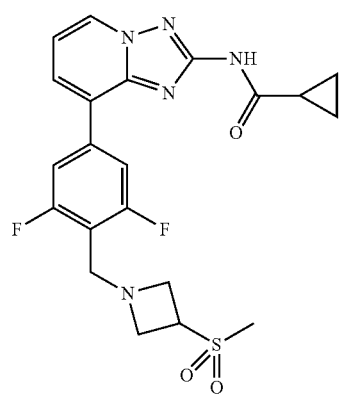 [SMILES: CS(=O)(=O)C1CN(Cc2c(F)cc(-c3cccn4nc(NC(=O)C5CC5)nc34)cc2F)C1]

It was prepared by referring to the method of Example 1.
MS (ESI): 462.14 (M+1)

Example 17. 8-(4-((3-(methylsulfonyl)azetidin-1-yl)methyl)phenyl)-[1,2,4]triazolo[1,5-a]pyridin-2-ylamine

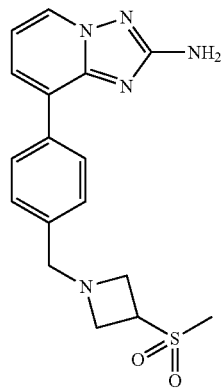 [SMILES: CS(=O)(=O)C1CN(Cc2ccc(-c3cccn4nc(N)nc34)cc2)C1]

It was prepared by referring to the method of Example 1.
MS (ESI): 358.13 (M+1)

Example 18. 8-(4-((3-(ethylsulfonyl)azetidin-1-yl)methyl)phenyl)-[1,2,4]triazolo[1,5-a]pyridin-2-ylamine

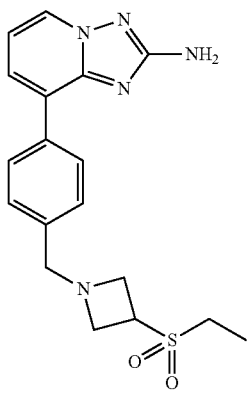 [SMILES: CCS(=O)(=O)C1CN(Cc2ccc(-c3cccn4nc(N)nc34)cc2)C1]

It was prepared by referring to the method of Example 1.
MS (ESI): 372.14 (M+1)

Example 19. 4-(4-(7H-pyrrolo[2,3-d]pyrimidin-4-yl)benzyl)thiomorpholine 1,1-dioxide

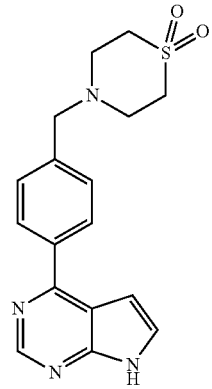 [SMILES: O=S1(=O)CCN(Cc2ccc(-c3ncnc4[nH]ccc34)cc2)CC1]

Step 1, 4-(4-(4,4,5,5-tetramethyl-1,3,2-dioxaborolan-2-yl)benzyl)thiomorpholine 1,1-dioxide

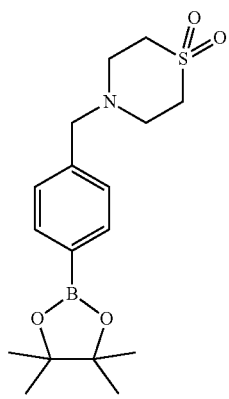 [SMILES: CC1(C)OB(c2ccc(CN3CCS(=O)(=O)CC3)cc2)OC1(C)C]

5 g of 2-(4-(bromomethyl)phenyl)-4,4,5,5-tetramethyl-1,3,2-dioxaborolane was added in a 100 ml three-neck round bottom glass bottle, and dissolved with 10 ml of N,N-dimethylformamide 5.8 g of potassium carbonate and 4 g of thiomorpholine 1,1-dioxide hydrochloride were then added, and reacted under nitrogen for 2 hours at room temperature. Thin layer chromatography indicated that the reaction was completed. Ice water was added to the reaction mixture, and extracted with ethyl acetate (25 ml×3). The organic layer was washed with water, dried (sodium sulfate), filtered and concentrated to give 6 g of desired product.

Step 2. 4-(4-(7-((2-(trimethylsilyl)ethoxy)methyl)-7H-pyrrolo[2,3-d]pyrimidin-4-yl)benzyl)thiomorpholine 1,1-dioxide

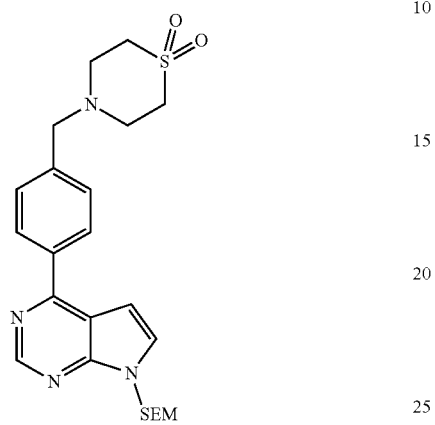

2 g of 4-chloro-7-((2-(trimethylsilyl)ethoxy)methyl)-7H-pyrrolo[2,3-d]pyrimidine, 2.7 g of the product of step 1, 1.0 g of potassium carbonate, and 0.3 g of Pd(dppf)Cl$_2$ were added in 30 ml of dioxane/water (5:1) and heated to 100° C. for 2 h. After filtration, the filtrate was rotary evaporated to dryness to remove the dioxane and diluted with water. After extracted with ethyl acetate, and purified by column chromatography, the title compound (1.8 g) was obtained.

Step 3. 4-(4-(7H-pyrrolo[2,3-d]pyrimidin-4-yl)benzyl)thiomorpholine 1,1-dioxide 3 g of the product of step 2 was dissolved in 15 ml of dichloromethane, and cooled to 0° C. in an ice bath. 5 ml of trifluoroacetic acid was added to the reaction mixture. After the addition, the ice bath was removed, and the reaction was resumed at room temperature. After 5 hours, thin layer chromatography showed that the reaction was completed. The solvent was removed by concentration under reduced pressure and dichloromethane was added. The residual trifluoroacetic acid was removed by rotary evaporation to give a yellow oil. The yellow oil was dissolved in 15 ml of methanol and cooled to 0° C. with an ice salt bath. To the reaction mixture, 3 ml of anhydrous ethylenediamine was added dropwise. After the addition was completed, the ice bath was removed and the mixture was allowed to react at room temperature overnight. The next day, the reaction was completed. The solid was precipitated, filtered, and purified by silica gel column chromatography to give 1.6 g of the object product.

$^1$HNMR (400 MHz, DMSO-D6) δ 12.06 (s, 1H), 8.83 (s, 1H), 8.17 (d, 2H), 7.66 (d, 1H), 7.55 (d, 2H), 6.90 (s, 1H), 3.78 (s, 2H), 3.15 (m, 4H), 2.93 (m, 4H).

MS (ESI): 343.12 (M+1)

Example 20. 4-(4-(7H-pyrrolo[2,3-d]pyrimidin-4-yl)benzyl)morpholine

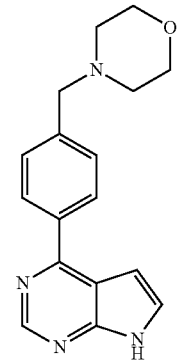 [SMILES: c1nc(-c2ccc(CN3CCOCC3)cc2)c2cc[nH]c2n1]

It was prepared by referring to the method of Example 19.

$^1$HNMR (400 MHz, DMSO-D6) δ 12.21 (s, 1H), 8.84 (s, 1H), 8.15 (d, 2H), 7.66 (d, 1H), 7.53 (d, 2H), 6.90 (d, 1H), 3.62-3.58 (m, 4H), 3.56 (s, 2H), 2.41 (s, 4H).

MS (ESI): 343.12 (M+1)

Example 21. 4-(4-((4-methylpiperazin-1-yl)methyl)phenyl)-7H-pyrrolo[2,3-d]pyrimidine

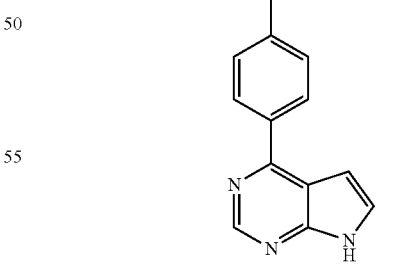

It was prepared by referring to the method of Example 19.

$^1$HNMR (400 MHz, CDCl$_3$) δ 12.31 (s, 1H), 9.01 (s, 1H), 8.11 (d, 2H), 7.52 (d, 2H), 7.43 (d, 1H), 7.53 (d, 2H), 6.85 (d, 1H), 3.62 (s, 4H), 2.55 (m, 8H), 2.33 (s, 3H).

Example 22. 1-(4-(7H-pyrrolo[2,3-d]pyrimidin-4-yl)benzyl)piperidin-4-one

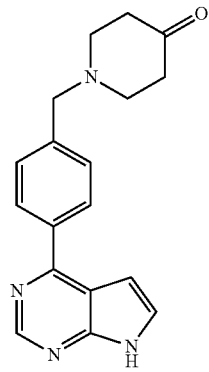 [SMILES: O=C1CCN(Cc2ccc(-c3ncnc4[nH]ccc34)cc2)CC1]

It was prepared by referring to the method of Example 19.

¹HNMR (400 MHz, DMSO-D6) δ 12.32 (s, 1H), 8.19 (d, 2H), 7.15 (d, 1H), 7.66 (d, 1H), 7.58 (d, 2H), 6.90 (d, 1H), 3.72 (s, 2H), 2.74 (t, 4H), 2.40 (t, 4H).

Example 23. 4-(4-(pyrrol-1-ylmethyl)phenyl)-7H-pyrrolo[2,3-d]pyrimidine

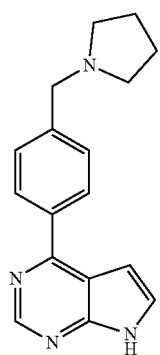

It was prepared by referring to the method of Example 19.

¹HNMR (400 MHz, DMSO-D6) δ 12.27 (s, 1H), 8.83 (s, 1H), 8.15 (d, 1H), 7.66 (d, 1H), 7.53 (d, 2H), 6.90 (m, 1H), 3.69 (s, 2H), 2.50-2.47 (m, 4H), 1.72 (s, 4H).

Example 24. 4-(4-(1H-pyrrolo[2,3-b]pyridin-4-yl)benzyl)thiomorpholine 1,1-dioxide

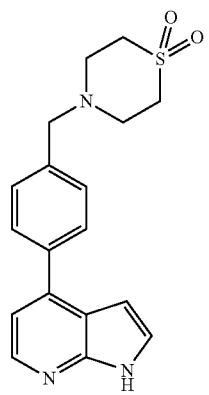 [SMILES: O=S1(=O)CCN(Cc2ccc(-c3ccnc4[nH]ccc34)cc2)CC1]

It was prepared by referring to the method of Example 19.

MS (ESI): 342.12 (M+1)

Example 25. 4-(4-(1H-pyrrolo[2,3-b]pyridin-3-yl)benzyl)thiomorpholine 1,1-dioxide

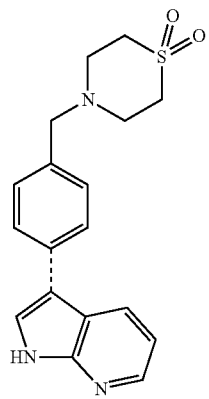

It was prepared by referring to the method of Example 19.

MS (ESI): 342.12 (M+1)

Example 26. 4-(4-(1H-pyrrolo[2,3-b]pyridin-3-yl)benzyl)morpholine

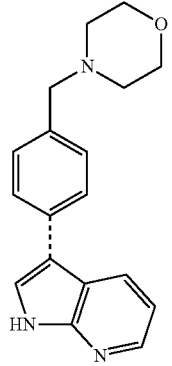

It was prepared by referring to the method of Example 19.

¹HNMR (400 MHz, DMSO-D6) δ 11.93 (s, 1H), 8.32-8.24 (m, 1H), 7.85 (s, 1H), 7.69 (d, 2H), 7.36 (d, 2H), 7.15 (m, 1H), 3.64-3.52 (m, 4H), 2.50-2.47 (m, 4H), 3.48 (s, 2H), 2.38 (s, 4H).

Example 27. 3-(4-((4-methylpiperazin-1-yl)methyl)phenyl)-7H-pyrrolo[2,3-b]pyridine

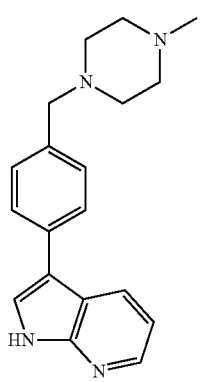 [SMILES: CN1CCN(Cc2ccc(-c3c[nH]c4ncccc34)cc2)CC1]

It was prepared by referring to the method of Example 19.

¹HNMR (400 MHz, DMSO-D6) δ 11.93 (s, 1H), 8.28 (m, 2H), 7.85 (s, 1H), 7.68 (d, 2H), 7.35 (d, 2H), 7.15 (m, 1H), 3.46 (s, 2H), 2.36 (brs, 8H), 2.15 (s, 3H).

Example 28. 4-(4-(1H-pyrrolo[2,3-b]pyridin-3-yl)benzyl)piperidin-4-one

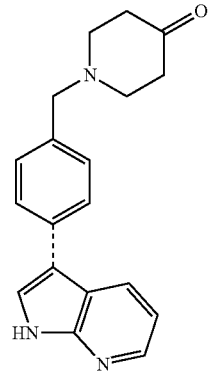

It was prepared by referring to the method of Example 19.

¹HNMR (400 MHz, DMSO-D6) δ 12.05 (s, 1H), 8.41 (m, 2H), 7.99 (d, 1H), 7.82 (d, 2H), 7.53 (d, 2H), 7.26 (dd, 1H), 3.72 (s, 2H), 2.81 (t, 4H), 2.47 (t, 4H).

Example 29. 3-(4-(pyrrol-1-ylmethyl)phenyl)-1H-pyrrolo[2,3-b]pyridine

It was prepared by referring to the method of Example 19.

¹HNMR (400 MHz, DMSO-D6) δ 11.92 (s, 1H), 8.27 (m, 2H), 7.84 (s, 1H), 7.65 (m, 2H), 7.35 (d, 2H), 7.15 (dd, 1H), 3.57 (s, 2H), 2.42 (dd, 4H), 1.69 (m, 4H).

Example 30. Inhibition of JAK

The study of the effect of compounds on the activity of purified recombinant JAK was performed by studying the inhibitory activity of the compounds on JAK from the enzymatic level. The experimental principle is to use a luminescence kinase assay to detect the ADP content produced by the reaction of JAK with the substrate Poly (4:1 Glu, Tyr) peptide: after ADP is converted to ATP, ATP can act as a substrate for the Ultra-Glo luciferase catalytic reaction, producing an optical signal. The luminescence signal is positively correlated with the amount of ADP and kinase activity. Therefore, the inhibitory effect of the compounds on the recombinant JAK was determined by observing the luminescence signal produced by the reaction of JAK and the substrate, and was expressed by $IC_{50}$.

Experimental method: 10 different concentrations of compounds were incubated with JAK1, JAK2 and JAK3, respectively, for 60 minutes at 37° C. The substrate and ATP were then added, mixed, and reacted at 37° C. for 50 minutes. 25 μl of ADP-Glo™ was added and mixed for 2 minutes. The reaction was carried out for 50 minutes at room temperature. Further, 50 μl of the detection reagent was added and mixed for 2 minutes, and incubated at room temperature for 50 minutes, and detected by a chemiluminometer. The results are shown in Table 1.

TABLE 1

Experimental results of inhibition of JAK

| Compound | Inhibition of JAK1 $IC_{50}(nM)$ | Inhibition of JAK2 $IC_{50}(nM)$ | Inhibition of JAK3 $IC_{50}(nM)$ |
| --- | --- | --- | --- |
| Example compound 1 | b | c | c |
| Example compound 2 | b | c | c |
| Example compound 3 | b | c | c |
| Example compound 5 | b | c | b |
| Example compound 6 | c | c | c |
| Example compound 7 | b | c | b |
| Example compound 8 | b | c | b |
| Example compound 9 | b | c | c |
| Example compound 10 | c | c | c |
| Example compound 11 | b | c | c |
| Example compound 12 | b | c | c |
| Example compound 13 | b | c | c |
| Example compound 14 | b | c | c |
| Example compound 15 | b | c | c |
| Example compound 16 | c | c | c |
| Example compound 17 | b | c | b |
| Example compound 18 | c | c | c |
| Example compound 19 | a | c | c |

Note:
1. (a) ≤20 nM;
2. (b) >20 nM to 50 nM;
3. (c) >50 nM

As an example, Example 1 was compared with the results of the existing JAK inhibitor under the same experimental conditions, and the results are shown in Table 2.

TABLE 2

Comparison of the inhibitory effects of the compounds disclosed herein and the existing JAK inhibitor on JAK

| Compound | Inhibition of JAK1 $IC_{50}$ (nM) | Inhibition of JAK2 $IC_{50}$ (nM) | Inhibition of JAK3 $IC_{50}$ (nM) |
| --- | --- | --- | --- |
| Example compound 1 | 48.0 | 498 | 2433 |
| Filgotinib | 46 | 55 | 644 |

The results showed that the inhibitory activity of the compound of Example 1 against JAK1 was 10 times that of JAK2, and the inhibitory activities of filgotinib (the compound disclosed in CN104262337) against JAK1 and JAK2 were comparable in this experiment, suggesting that the compounds disclosed herein have better selectivity for JAK1 and thus have lower toxicity.

What is claimed is:
1. A compound of formula (I):

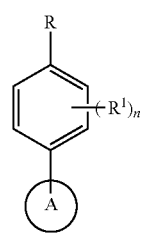

Formula (I)

and an isomer, a solvate, or a pharmaceutically acceptable salt thereof,
when

is selected from:

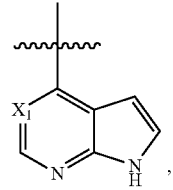

wherein, $X_1$ is N;
R is selected from:

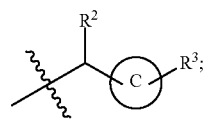

wherein:

is a 4-10 membered nitrogen-containing heterocycle wherein the carbon atom can be replaced by O, S, or —$SO_2$—;
$R^1$ is hydrogen, $C_1$-$C_6$ alkyl, or halogen;
$R^2$ is hydrogen or $C_1$-$C_3$ alkyl;
$R^3$ is hydrogen, $C_1$-$C_3$ alkyl, or $C_1$-$C_6$ alkylsulfonyl;
n is selected from 0, 1, 2;

when

is selected from:

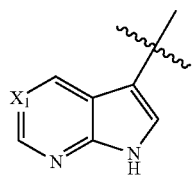

Wherein, $X_1$ is CH or N;
R is selected from:

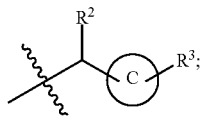

wherein:

is a 4-10 membered nitrogen-containing heterocycle wherein the carbon atom can be replaced by O, S, or —SO$_2$—;
$R^1$ is hydrogen, $C_1$-$C_6$ alkyl, or halogen;
$R^2$ is hydrogen or $C_1$-$C_3$ alkyl;
$R^3$ is hydrogen, $C_1$-$C_3$ alkyl, or $C_1$-$C_6$ alkylsulfonyl;
n is selected from 0, 1, 2;
when

is selected from:

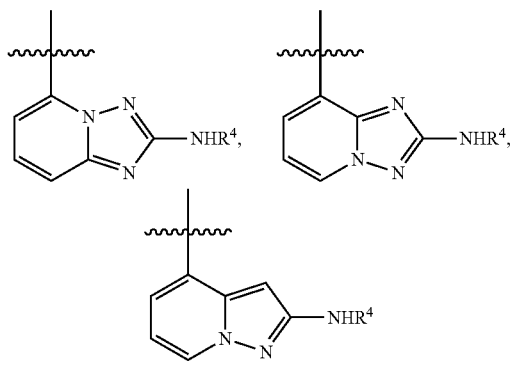

R is selected from:

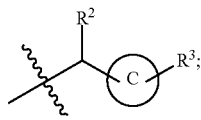

wherein:

is selected from:

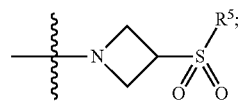

$R^1$ is hydrogen, $C_1$-$C_6$ alkyl, or halogen;
$R^2$ is hydrogen or $C_1$-$C_3$ alkyl;
$R^3$ is hydrogen, $C_1$-$C_3$ alkyl, or $C_1$-$C_6$ alkylsulfonyl;
$R^4$ is hydrogen, $C_1$-$C_7$ alkylacyl, $C_3$-$C_7$ cycloalkylacyl, or a $C_1$-$C_6$ alkylsulfonyl, and may be optionally substituted by $C_1$-$C_6$ alkoxy, $C_1$-$C_6$ alkylsulfonyl, or halogen;
$R^5$ is selected from $C_1$-$C_5$ alkyl, $C_3$-$C_7$ cycloalkyl, and may be optionally substituted by halogen;
n is selected from 0, 1, 2.

2. The compound according to claim 1, wherein said compound has the following structure:
N-(5-(4-((3-(methylsulfonyl)azetidin-1-yl)methyl)phenyl)-[1,2,4]triazolo[1,5-a]pyridin-2-yl]cyclopropanecarboxamide;
N-(5-(3-fluoro-4-((3-(methylsulfonyl)azetidin-1-yl)methyl)phenyl)-[1,2,4]triazolo[1,5-a]pyridin-2-yl]cyclopropanecarboxamide;
N-(5-(3,5-difluoro-4-((3-(methylsulfonyl)azetidin-1-yl)methyl)phenyl)-[1,2,4]triazolo[1,5-a]pyridin-2-yl]cyclopropanecarboxamide;
N-(5-(4-((3-(methylsulfonyl)azetidin-1-yl)methyl)phenyl)-[1,2,4]triazolo[1,5-a]pyridin-2-yl]isobutyramide;
N-(5-(4-((3-(cyclopropylsulfonyl)azetidin-1-yl)methyl)phenyl)-[1,2,4]triazolo[1,5-a]pyridin-2-yl]isobutyramide;
N-(5-(4-((3-(ethylsulfonyl)azetidin-1-yl)methyl)phenyl)-[1,2,4]triazolo[1,5-a]pyridin-2-yl]isobutyramide;
N-(5-(4-((3-(ethylsulfonyl)azetidin-1-yl)methyl)phenyl)-[1,2,4]triazolo[1,5-a]pyridin-2-yl]cyclopropanecarboxamide;
5-(4-((3-(methylsulfonyl)azetidin-1-yl)methyl)phenyl)-[1,2,4]triazolo[1,5-a]pyridin-2-ylamine;
N-(8-(4-((3-(methylsulfonyl)azetidin-1-yl)methyl)phenyl)-[1,2,4]triazolo[1,5-a]pyridin-2-yl]cyclopropanecarboxamide;
N-(8-(4-((3-(cyclopropylsulfonyl)azetidin-1-yl)methyl)phenyl)-[1,2,4]triazolo[1,5-a]pyridin-2-yl]cyclopropanecarboxamide;
N-(8-(4-((3-(ethylsulfonyl)azetidin-1-yl)methyl)phenyl)-[1,2,4]triazolo[1,5-a]pyridin-2-yl]cyclopropanecarboxamide;
N-(8-(4-((3-(methylsulfonyl)azetidin-1-yl)methyl)phenyl)-[1,2,4]triazolo[1,5-a]pyridin-2-yl]cyclopropanecarboxamide;

N-(8-(4-((3-(cyclopropylsulfonyl)azetidin-1-yl)methyl) phenyl)-[1,2,4]triazolo[1,5-a]pyridin-2-yl]isobutyramide;

N-(8-(4-((3-(ethylsulfonyl)azetidin-1-yl)methyl)phenyl)-[1,2,4]triazolo[1,5-a]pyridin-2-yl]isobutyramide;

N-(8-(3-fluoro-4-((3-(methylsulfonyl)azetidin-1-yl)methyl)phenyl)-[1,2,4]triazolo[1,5-a]pyridin-2-yl]cyclopropanecarboxamide;

N-(8-(3,5-difluoro-4-((3-(methylsulfonyl)azetidin-1-yl)methyl)phenyl)-[1,2,4]triazolo[1,5-a]pyridin-2-yl]cyclopropanecarboxamide;

8-(4-((3-(methylsulfonyl)azetidin-1-yl)methyl)phenyl)-[1,2,4]triazolo[1,5-a]pyridin-2-ylamine;

8-(4-((3-(ethylsulfonyl)azetidin-1-yl)methyl)phenyl)-[1,2,4]triazolo[1,5-a]pyridin-2-ylamine;

4-(4-(7H-pyrrolo[2,3-d]pyrimidin-4-yl)benzyl)thiomorpholine 1,1-dioxide;

4-(4-(7H-pyrrolo[2,3-d]pyrimidin-4-yl)benzyl)morpholine;

4-(4-((4-methylpiperazin-1-yl)methyl)phenyl)-7H-pyrrolo[2,3-d]pyrimidine;

1-(4-(7H-pyrrolo[2,3-d]pyrimidin-4-yl)benzyl)piperidin-4-one;

4-(4-(pyrrol-1-ylmethyl)phenyl)-7H-pyrrolo[2,3-d]pyrimidine;

4-(4-(1H-pyrrolo[2,3-b]pyridin-4-yl)benzyl)thiomorpholine 1,1-dioxide;

4-(4-(1H-pyrrolo[2,3-b]pyridin-3-yl)benzyl)thiomorpholine 1,1-dioxide;

4-(4-(1H-pyrrolo[2,3-b]pyridin-3-yl)benzyl)morpholine;

3-(4-((4-methylpiperazin-1-yl)methyl)phenyl)-7H-pyrrolo[2,3-b]pyridine;

4-(4-(1H-pyrrolo[2,3-b]pyridin-3-yl)benzyl)piperidin-4-one, or 3-(4-(pyrrol-1-ylmethyl)phenyl)-1H-pyrrolo[2,3-b]pyridine;

and an isomer, a solvate or a pharmaceutically acceptable salt thereof.

3. A pharmaceutical composition, comprising
a compound, isomer, solvate or pharmaceutically acceptable salt thereof according to claim 1, and
pharmaceutically acceptable carriers.

4. A pharmaceutical composition, comprising
a compound, isomer, solvate or pharmaceutically acceptable salt thereof according to claim 2, and
pharmaceutically acceptable carriers.

5. A method of treating a patient suffering from a disease associated with JAK kinase, comprising administering to the patient a compound according to claim 1.

6. A method of treating a patient suffering from a disease associated with JAK kinase, comprising administering to the patient a compound according to claim 2.

7. The method of claim 5, wherein the said disease is selected from autoimmune disease, rheumatoid arthritis, skin condition, multiple sclerosis, psoriatic arthritis, inflammatory bowel disease, myasthenia gravis, and psoriasis.

8. The method of claim 6, wherein the said disease is selected from autoimmune disease, rheumatoid arthritis, skin condition, multiple sclerosis, psoriatic arthritis, inflammatory bowel disease, myasthenia gravis, and psoriasis.

* * * * *